United States Patent [19]

Tollini

[11] Patent Number: 5,195,957
[45] Date of Patent: Mar. 23, 1993

[54] STERILANT CARTRIDGE-CAP AND ASSOCIATED CONNECTION

[76] Inventor: Dennis R. Tollini, 19 Palmdale Dr., Williamsville, N.Y. 14221

[21] Appl. No.: 753,407

[22] Filed: Aug. 30, 1991

Related U.S. Application Data

[63] Continuation-in-part of Ser. No. 650,406, Feb. 1, 1991, abandoned.

[51] Int. Cl.⁵ .............................................. A61M 3/00
[52] U.S. Cl. ...................................... 604/29; 604/256; 604/905
[58] Field of Search ............... 604/29, 212, 256, 283, 604/905

[56] References Cited

U.S. PATENT DOCUMENTS

| | | |
|---|---|---|
| 2,636,644 | 4/1953 | Taylor .................................. 604/212 |
| 2,727,516 | 12/1955 | Lockhart . |
| 4,022,206 | 5/1977 | Hilleman et al. .................... 604/212 |
| 4,417,890 | 11/1983 | Dennehey et al. .................. 604/256 |
| 4,431,424 | 2/1984 | Svensson ............................. 604/33 |
| 4,432,764 | 2/1984 | Lopez .................................. 604/283 |
| 4,432,766 | 2/1984 | Bellotti et al. ...................... 604/283 |
| 4,439,188 | 3/1984 | Dennehey et al. .................. 604/29 |
| 4,440,207 | 4/1984 | Genatempo et al. ............... 150/52 R |
| 4,551,146 | 11/1985 | Rogers ................................. 604/403 |
| 4,588,402 | 5/1986 | Igari et al. ........................... 604/905 |
| 4,624,664 | 11/1986 | Peluso et al. ........................ 604/256 |
| 4,642,091 | 2/1987 | Richmond ........................... 604/283 |
| 4,738,668 | 4/1988 | Bellotti et al. ...................... 604/29 |
| 4,778,447 | 10/1988 | Velde et al. ......................... 604/29 |
| 4,983,161 | 1/1991 | Dadson et al. ...................... 604/905 |
| 5,053,003 | 10/1991 | Dadson et al. ...................... 604/29 |

Primary Examiner—Stephen C. Pellegrino
Assistant Examiner—Ralph A. Lewis
Attorney, Agent, or Firm—Joseph P. Gastel

[57] ABSTRACT

A sterilant cartiridge-cap for use in peritoneal dialysis and other inline sterilant delivery applications including an elongated flexible tubular clear body member of substantially uniform cross section closed at one end and having a clear male Luer connector on its opposite end for attachment to an associated female Luer member at the end of the tube such as an extension set connected to a tube protruding form a patient's body, an O-ring on the female Luer member for engagement between such shoulder and a rim of a collar on the mal Luer member, sterilant liquid in the tubular body member, and an air bubble in the sterilant liquid. The male and female portions of the Luer connectors provide an inner seal, and the rim of the male member provides an outer seal with the O-ring. During detachment of the male and female members, the inner seal is broken before the outer seal is broken, and the volume between the male and female members increases as they move apart while the outer seal is maintained. The movement apart creates a vacuum in the female member which causes sterillant to automatically be drawn into it from the cartridge cap while the outer seal prevents air from being drawn into the Luer connector from the environment.

22 Claims, 6 Drawing Sheets

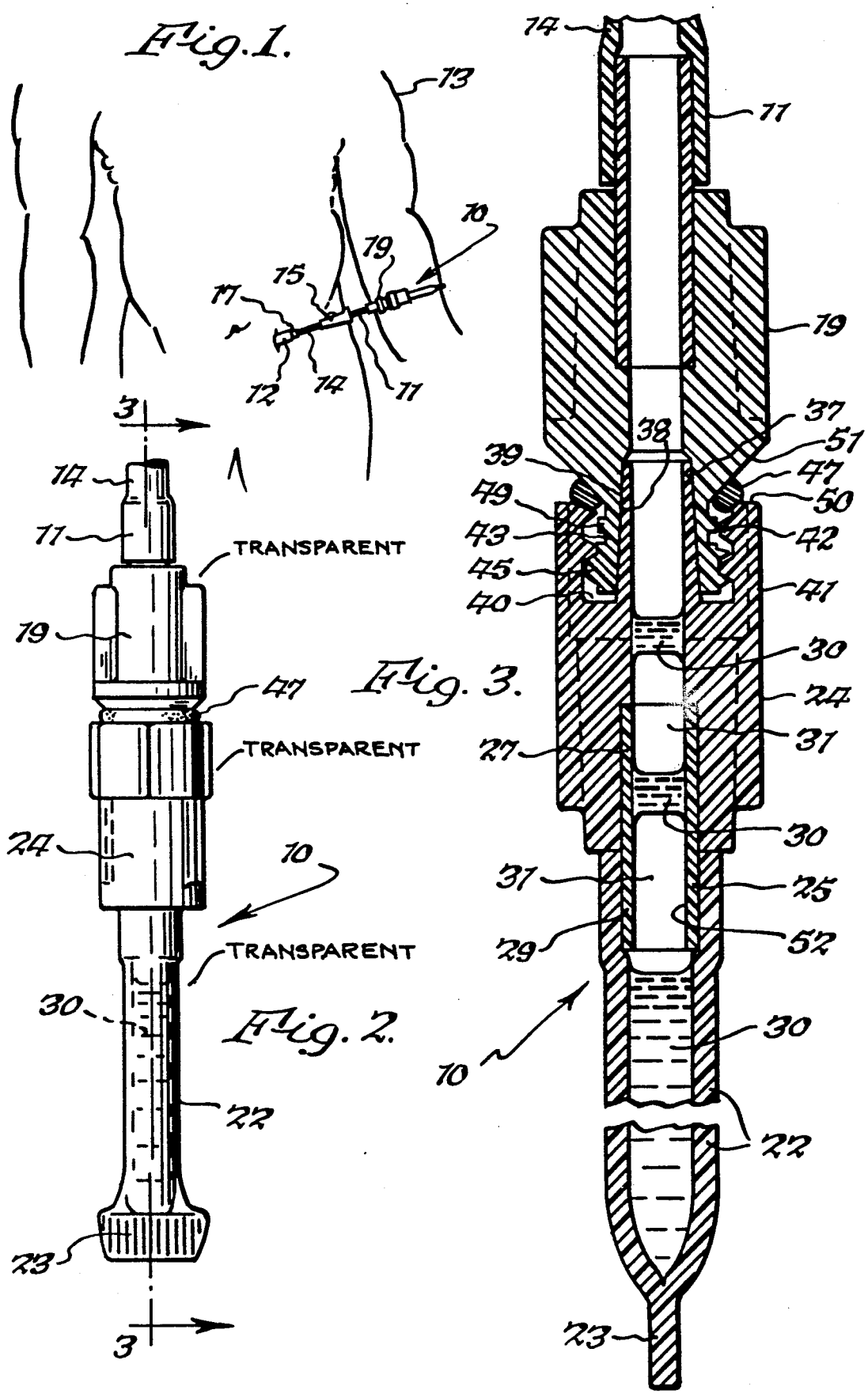

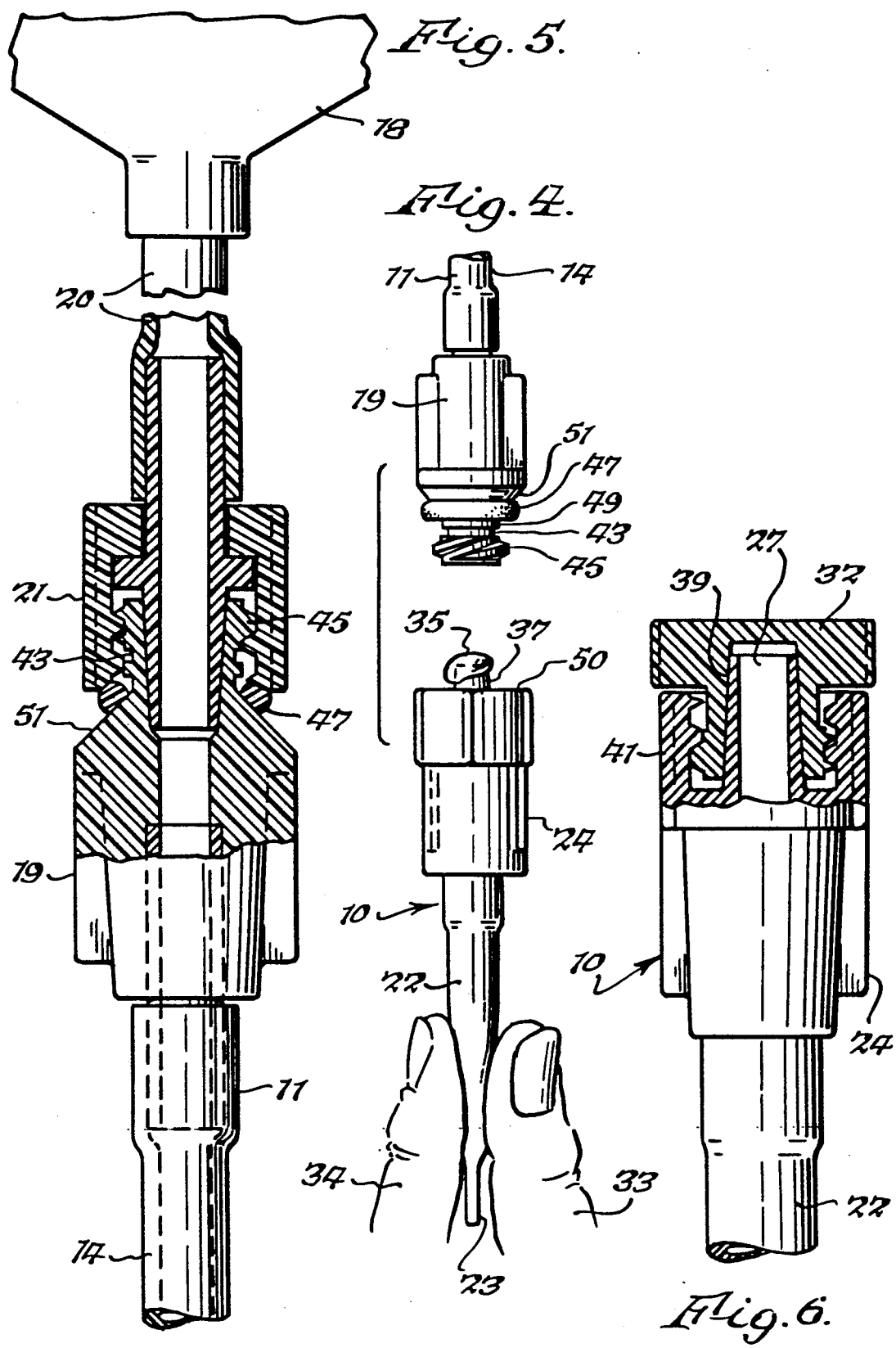

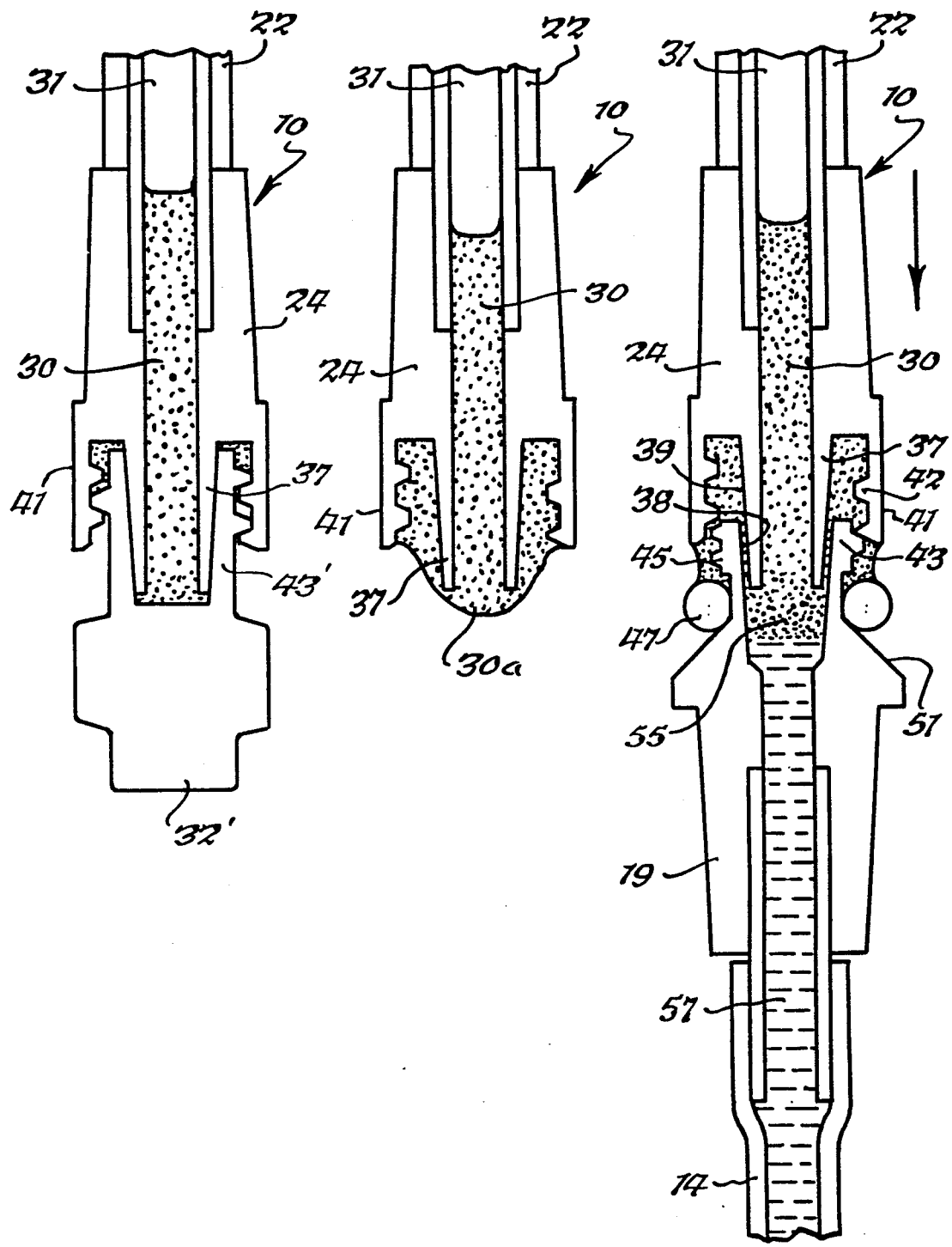

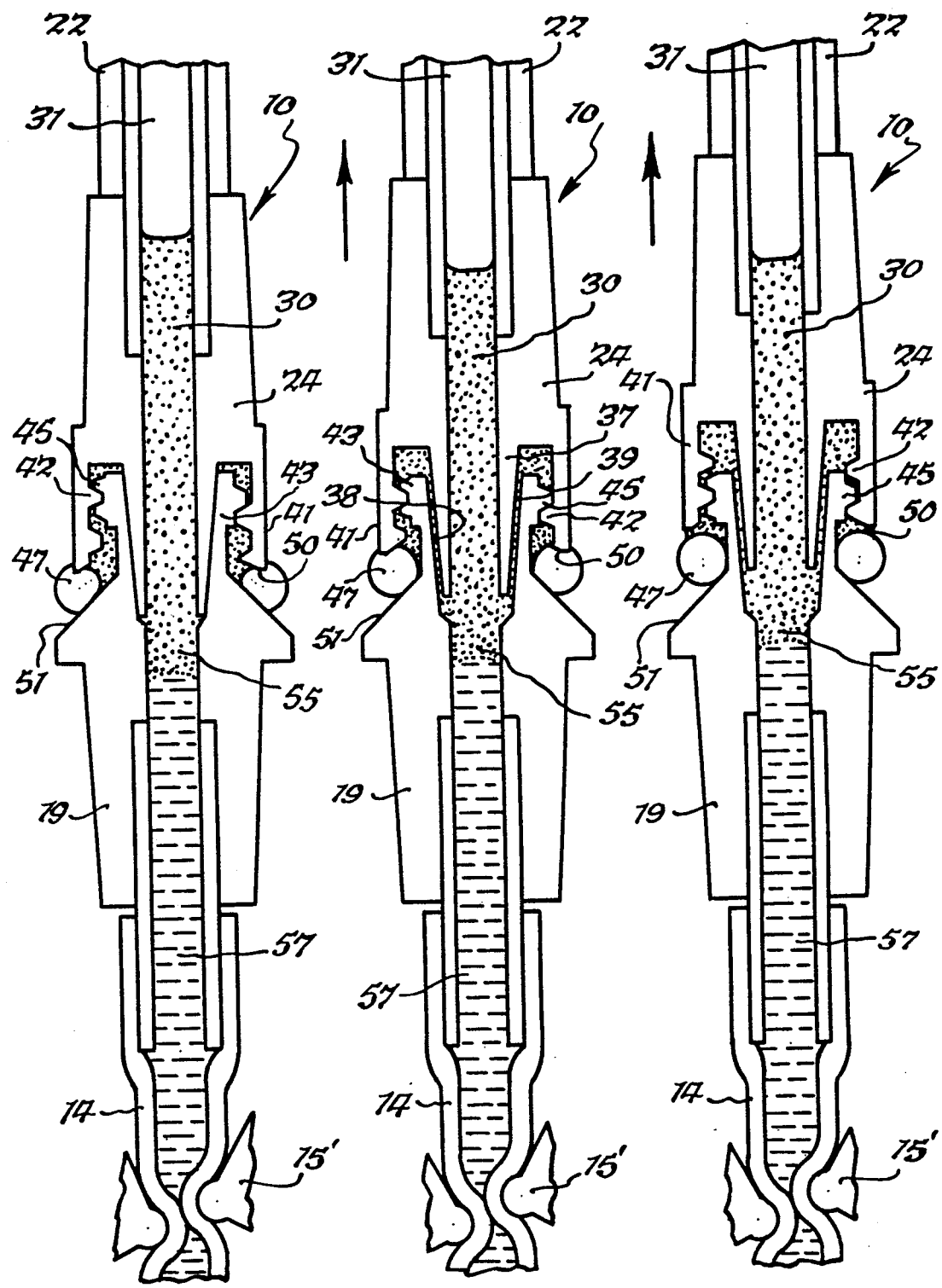

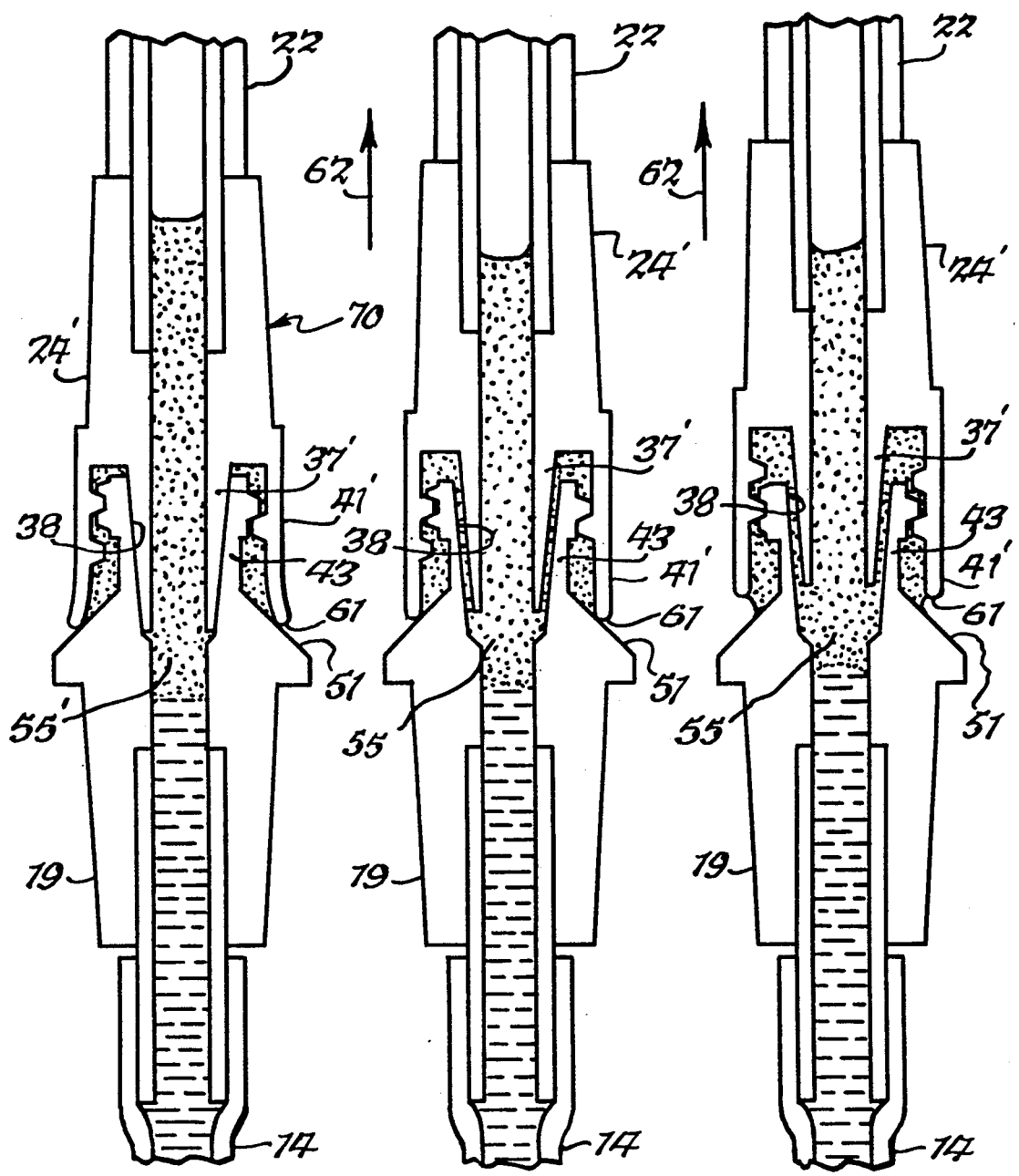

STERILANT CARTRIDGE-CAP AND ASSOCIATED CONNECTION

CROSS REFERENCE TO RELATED APPLICATION

The present application is a continuation-in-part of application Ser. No. 650,406, filed Feb. 1, 1991.

BACKGROUND OF THE INVENTION

The present invention relates to a sterilant cartridge-cap and an associated connection for an extension set utilized in peritoneal dialysis and for other inline sterilant delivery applications where asepsis is desired.

By way of background, in peritoneal dialysis a tube, known as a Tenckhoff catheter, protrudes from the abdomen of a patient, and an extension set is attached thereto through which dialysis fluid is periodically infused into the peritoneum. However, in periods between infusion, the end of the extension set is capped to protect it from contamination. In the past various types of caps have been utilized for the combined capping the end of the extension set and injecting sterilant into the end thereof. Certain caps of this type are disclosed in U.S. Pat. No. 4,432,764.

SUMMARY OF THE INVENTION

It is one object of the present invention to provide an improved sterilant cartridge-cap for mounting on a tube such as an extension set utilized in peritoneal dialysis and for other inline sterilant applications where asepsis is desired, the cap containing sterilant and being initially squeezed before it is connected to the tube to dispense sterilant onto the internal connector parts of the cap and being thereafter additionally squeezed after it is connected to the tube to inject sterilant fluid into the end thereof.

It is another object of the present invention to provide an improved sterilant cartridge-cap for mounting on a tube, especially an extension set utilized in peritoneal dialysis and other applications where sterilization is extremely important, the cartridge-cap containing structure which automatically causes an infusion of sterilant into the connector to the tube incidental to the detachment of the cartridge-cap therefrom, thereby insuring that sterilization is obtained.

It is still another object of the present invention to provide an improved sterilant cartridge-cap which has a clear flexible body containing clear substantially colorless sterilant with an air bubble therein and a clear connector so that the passage of sterilant through the clear body and the connector can be observed when the flexible body is squeezed, to thus confirm the flow of the sterilant.

A further object of the present invention is to provide an improved sterilant cartridge-cap and tube combination which will provide an extremely leak-proof seal when they are connected.

Yet another object of the present invention is to provide a sterilant cartridge-cap and tube combination which can be coupled and decoupled extremely simply with little force but yet will maintain a positive assembled relationship.

Still another object of the present invention is to provide a sterilant cartridge-cap having an elongated flexible body so that it will fit trimly against the patient's body and not project excessively through clothing which covers it or be abrasive to the patient's body.

A still further object of the present invention is to provide a sterilant cartridge cap which can be used by patients who may not have optimum manual dexterity. Other objects and attendant advantages of the present invention will readily be perceived hereafter.

The present invention relates to a sterilant cartridge-cap comprising a flexible tubular body member of substantially uniform cross section having first and second ends, sidewall means on said flexible tubular member for receiving digital pressure, means sealing said first end, connector means on said second end for attachment to an associated member, and sterilant liquid means in said tubular body member for transfer to said associated member upon the application of said digital pressure to said sidewall means.

The present invention also relates to a sterilant cartridge-cap connector assembly comprising a sterilant cartridge cap including a tubular body member having first and second ends, flexible sidewall means on said tubular body member for receiving digital pressure, means sealing said first end, first connector means on said second end, second connector means for attachment to said first connector means, sterilant liquid means in said tubular body member for transfer to said second connector means upon the application of said digital pressure to said flexible sidewall means, inner seal means for providing a first seal between said first and second connector means, and outer seal means for providing a second seal between said first and second connector means when said first connector means is mounted onto said second connector means, said inner and outer seal means being dimensioned to maintain said second seal closed while said first seal is being opened during uncoupling of said first and second connector means to thereby cause a flow of said sterilant liquid means from said first connector means into said second connector means as a result of a vacuum created proximate said inner seal means during said uncoupling.

The various aspects of the present invention will be more fully understood when the following portions of the specification are read in conjunction with the accompanying drawings wherein:

BRIEF DESCRIPTION OF THE DRAWINGS

FIG. 1 is a view of the sterilant cartridge-cap of the present invention mounted on an extension set coupled to the life line catheter which protrudes from the abdomen of a peritoneal dialysis patient;

FIG. 2 is a fragmentary enlarged plan view of the sterilant cartridge-cap of the present invention mounted on the end of the extension set;

FIG. 3 is a further enlarged fragmentary cross sectional view taken substantially along line 3—3 of FIG. 2;

FIG. 4 is a fragmentary exploded view of the assembly of FIG. 2 and showing the manner in which a drop of sterilant liquid is squeezed from the sterilant cartridge-cap to coat the portions of the male Luer connector prior to mounting it on its female counterpart at the end of the extension set;

FIG. 5 is an enlarged fragmentary plan view, partially in cross section, of the female end of the extension set attached to a tube which conducts dialysis fluid thereto from a suitable source;

FIG. 6 is a fragmentary enlarged view, partially in cross section, showing a cap mounted on the end of the sterilant cartridge cap for retaining the sterilant fluid therein prior to mounting the cap onto the end of the extension set;

FIG. 7 is a fragmentary schematic drawing similar to FIG. 6 showing the sterilant-cartridge cap of the present invention with sterilant therein and with a closure cap thereon;

FIG. 8 is a fragmentary schematic drawing showing how the sterilant may flow out of the male end of the sterilant-cartridge cap after the closure cap thereon is removed and the body of the cartridge cap is squeezed;

FIG. 9 is a fragmentary schematic drawing showing the initial state of the sterilant-cartridge cap being mounted on the extension set;

FIG. 10 is a fragmentary schematic drawing showing the sterilant-cartridge cap fully mounted on the end of the extension set;

FIG. 11 is a fragmentary schematic drawing showing the ejection of sterilant from the sterilant-cartridge cap into the female Luer connector during the initial stage of the detachment of the sterilant-cartridge cap therefrom;

FIG. 12 is a fragmentary schematic drawing showing the end of the sterilant cartridge cap after it loses contact with the O-ring on the connector at the end of the extension set;

FIG. 14 is a fragmentary line schematic drawing of an embodiment which utilizes a soft flexible collar instead of an O-ring to provide an outer seal on a Luer connector which is shown in double-sealed relationship;

FIG. 15 is a view similar to FIG. 14 but showing the Luer connector with the inner seal opened but the outer seal still closed;

FIG. 16 is a view similar to FIG. 15 but showing both seals opened; and

DESCRIPTION OF THE PREFERRED EMBODIMENTS

Figure 13:
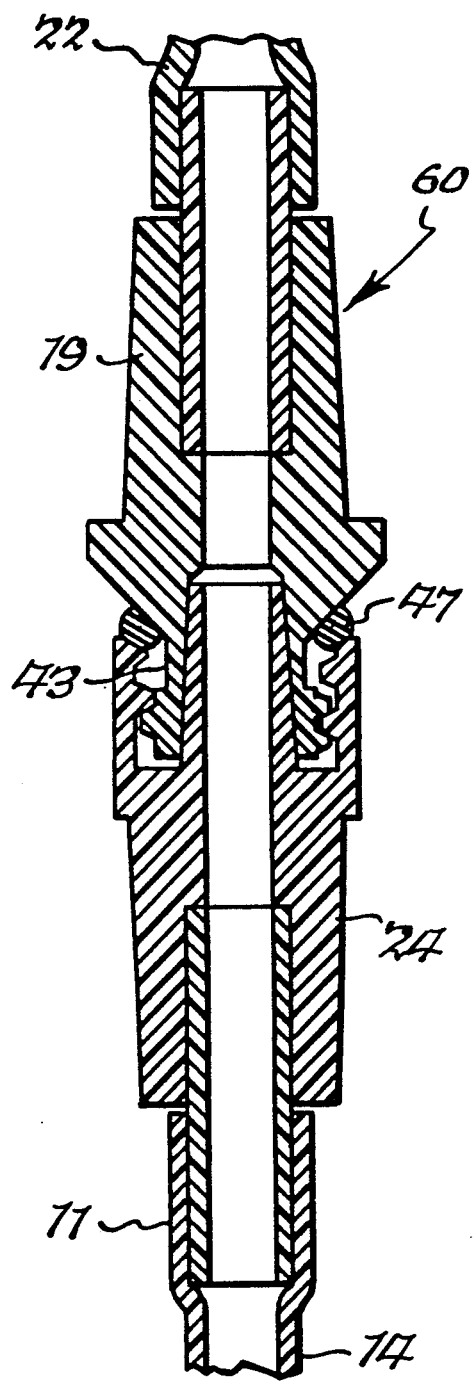
FIG. 13 is a fragmentary cross-sectional view of a modified embodiment of the present invention wherein the female Luer member and the sealing ring are a part of the cartridge cap.

In FIG. 1 the sterilant cartridge-cap 10 is shown as being mounted on one end of an extension set 11 used in peritoneal dialysis, the other end of which is mounted on a Tenckhoff catheter 12 which protrudes from the abdomen of a peritoneal dialysis patient 13. However, while the following description is specifically directed to peritoneal dialysis, it will be appreciated that it can be used with any other type of tube which requires inline sterilant delivery or connections where asepsis is required.

The extension set 11 includes a central flexible tube 14 having a conventional roller-type clamp 15 thereon but any other type of clamp can be used. It also includes a suitable Luer connector 17 which secures one end of the extension set to Tenckhoff catheter adapter 12, and at its opposite end it includes a modified Luer connector or member 19, which will be described in detail hereafter, to which the sterilant cartridge-cap 10 is attached. Broadly, the modification of FIGS. 1-6 consists of adding an annular ridge 49 and an O-ring 47 to connector 19.

As is well understood, the assembly of the extension set with the sterilant cartridge-cap 10 mounted thereon is worn by the patient between the dialysis infusions which are performed four times daily in most cases. During such infusions a tube 20 (FIG. 5) which is connected to a container 18 of dialysis fluid, has a connector 21 which is secured to the modified Luer connector 19 of the extension set 11. After the infusion has been completed, the connector portion 21 (FIG. 5) of the infusion tube 20 is disconnected from the extender set connector 19, and the sterilant cartridge-cap 10 of the present invention is mounted onto the end connector 19 of the extension set 11 to cap it off and apply sterilant to the end portion of the extension set and especially to the joint between connector 19 and connector 24 of the cap 10. At this point it is to be noted that the tubing 14 of the extension set is extremely soft and pliable as is the tubular body portion 22 of the sterilant cartridge-cap which extends beyond the connector end 24 thereof so that the assembly of parts 10 and 11 can be placed trimly against the abdomen of the patient and thus not protrude to any great extent.

The sterilant cartridge-cap 10 includes a flexible tubular body portion 22 having a sidewall of clear polyvinyl chloride of soft Durometer, and it is softer than extender tube 14, in the sense that it is more easily compressible. By way of example and not limitation, in a specific embodiment tubular body portion 22, which is easily compressed by digital pressure has a Durometer of 70 and tube 14 has a Durometer of 85. The tubular body portion 22 is conventional tubing of about ¼ inch outer diameter. The end 23 has a RF seal which may be ¼ of an inch long to insure complete closure. However, it can be blow-molded with a closed end or made in any other suitable manner. The main consideration is that it should be soft and flexible with a closure of any suitable type at its distal end. Furthermore, the tubular body portion can be made of any suitable material which, by way of example and not limitation, can be polyolefin, rubber, FDA approved silicone, etc. The end of body member 22 opposite sealed end 23 mounts a clear transparent conventional male Luer connector 24. In this respect, a rigid clear transparent tube 25 has an end 27 sealed by solvent bonding within connector 24 and the opposite end 29 has the end of tubular body member 22 mounted thereon in suitably sealed relationship by solvent bonding. Alternatively, tube 25 may be eliminated and the outside of tube 22 can be solvent bonded to the inside of connector 24. A suitable volume, such as one milliliter of sterilant 30 is contained within tubular body portion 22 which has sufficient volume so that one or more air bubbles 31 are also present within tubular member 22. The air bubble or bubbles 31 may be located anywhere in tubular portion 22 and connector 24 depending on the combination of the attitude of portion 22, the amount it has been shaken, and the viscosity of the liquid. The cap 10 has a cap 32 (FIG. 6) mounted thereon for the purpose of sealing the liquid and air bubbles therein prior to the time that the cartridge cap is placed in use by mounting it onto connector 19 of the extension set. One sterilant 30 which can be used is a clear substantially colorless liquid known under the trade name AMUCHINA and the sidewall of body member 22 is also clear transparent plastic so that the sterilant and the air bubble therein can be viewed therethrough. It will be appreciated that any FDA or 510K approved sterilant can be used. The specific entire cartridge-cap 10 including connector 24 is about 2¼ inches long. There is a total of about ¼ inch of air in the cap 10, and the remainder is sterilant. However, it will be appreciated that connector 24 can be longer or shorter than 2¼ inches to give a desired appropriate dose for the type of sterilant which is used, and the air within the cartridge cap should comprise about 10% of its volume.

As noted above, the sterilant cartridge-cap 10 is used to cap off the end of the extension set 11 after the latter has been used for an infusion of dialysis liquid and after the tube 20 has been detached therefrom. Prior to mounting the cap 10 onto connector 19, which is a modified conventional female clear transparent Luer connector, the cap 32 (FIG. 6) is removed and the soft flexible body member 22 is squeezed between the thumb 33 and forefinger 34 to force a few drops 35 of sterilant from the male portion 37 of the Luer connector 24. However, the Luer connector need not be transparent. These drops will thus flow onto and coat the outside surface 39 of the male portion 37 and will also flow into the annular chamber 40 between male portion 37 and annular collar 41 which has a double internal thread 42 therein. Thus, when the male end 37 is inserted into the tubular extension 43 of the female Luer connector 19, the mating parts will be coated by the sterilant. Additionally, the sterilant in chamber 40 and on threads 42 will coat the double male thread 45 to thus effect sterilization of these members also.

Because the engaging threads 42 and 45 are double threads, a rapid axial movement of connector 24 will be effected onto connector 19. A sealing ring in the form of an O-ring 47 is mounted on the neck 43 and is retained against moving off of neck 43 by an annular ridge 49. However, as will be seen in certain embodiments, ridge 49 is not used, as the threads on the neck can serve this purpose. O-ring 47 is preferably ⅛" in cross section and it fits with a slight interference fit onto neck 43 before connector 24 is screwed onto connector 19, as shown in FIG. 9. At this point it is to be again noted, and as explained in greater detail hereafter, that the O-ring 47 in combination with the frustoconical portion 51 of the connector and the annular rim 50 constitute a present improvement of the otherwise known female Luer connector 19 of the conventional extension set 11. In the foregoing respect, when connector 24 is screwed onto threads 45, the annular rim 50 will press against resilient O-ring 47 which is stretched and moved along onto and held against frustoconical connector portion 51 (FIG. 3). When connector 24 is unscrewed, O-ring 47 will contract and slide down frustoconical portion 51 and move back against ridge 49, as explained in greater detail hereafter. The compression of O-ring 47 between rim 50 and connector portion 51 performs a plurality of functions. First of all, it prevents over-tightening so that connector 24 can be unscrewed easily. Furthermore, the compression of O-ring 47 insures a good seal, and, further, by providing a resilience against rim 50, it prevents unscrewing, considering that the double thread can be unscrewed very easily, and this is especially possible considering that the connector is subjected to contact with the patient's clothing and body which may move relative thereto as the patient moves about.

As noted above, the specific AMUCHINA sterilant liquid 30 is clear and substantially colorless, and there are one or more air bubbles 31 within body member 22. However, as noted above, the sterilant need not be clear. The air bubble or bubbles serve a plurality of functions. First of all, as the sidewall of body member 22 is squeezed, as shown in FIG. 4, the air bubble or bubbles will break into a plurality of smaller bubbles and move toward and through the male portion 37 to provide a visual indication, when member 22 is transparent, that sterilant liquid is being ejected. Furthermore, it has been found that the existence of the air bubbles permit the liquid to pass more freely through the inside 52 of tube 25 and through the inside of male member 37 than if the sterilant completely fills the body member 22 and tube 25. Additionally, as noted above, connectors 24 and 19 are clear transparent plastic, as is extender tube 14. Thus, the travel of liquid through these parts can be observed, because of the movement of air bubbles, to insure that sufficient sterilant liquid 30 passes into the end of tube 14 to effect proper sterilization. Additionally, the existence of O-ring 47 prevents undesired leakage of sterilant fluid from the joint between connector portions 19 and 24 if for any reason there is not a good tight connection between the outside surface 39 of male portion 37 and the internal surface 38 of connector 19. An advantage of using clear sterilant is that the insides of connector members 19, 20 and 24 and the end of tube 14 will not become stained, as would be the case with BETADINE solution, and thus complete visibility of the passage of the fluid through the connector portions 19 and 24 will not be obscured. However, as noted above, any type of sterilant, including BETADINE, may be used if desired. Additionally, because the sidewall of tubular body portion 22 is flexible and resilient, after it has been released from a digital squeezing action, the sterilant will be pulled back into it to some extent so that a relatively large amount does not remain in the extension set.

In FIGS. 7-12 a sequence of actions is depicted for the movement of the sterilant from the time that the closure cap 32' is removed from its closed position on the cartridge cap (FIG. 7) until the sterilant cartridge cap 10 is removed from the end of the female Luer lock 19 on tube 14 (FIG. 12). All the numerals in FIGS. 7-12 correspond to the numerals previously used in FIGS. 1-6 except for the closure cap 32' which is a variant form of a closure cap 32 of FIG. 6 and except for the tube clamp 15' which is a fragmentary showing of a variant of the roller clamp 15 of FIG. 1. It is to be especially noted that the embodiment of FIGS. 7-12 does not have an annular ridge, such as 49 of FIGS. 1-6, and thus the O-ring 47 can move further onto neck 43. It is the threads 45 which retain it against movement off of neck 43.

In FIG. 7 the sterilant cartridge cap 10 is shown with closure cap 32' in fully seated position thereon and with sterilant 30 with an air bubble 31 therein. For facilitating the following explanation, sterilant 30 is depicted by stipling. In FIG. 8 the cartridge cap 10 is shown with the closure cap 32' removed from the male portion 37 of Luer connector 24. After removal of closure cap 32' a small amount of sterilant 30a (FIG. 8) can be ejected from the male end 37 of the Luer connector 24 by digital pressure, as noted above relative to FIG. 4. Air bubble 31 may be located anywhere in tubular portion 22. During handling of member 10, if there were originally a plurality of bubbles 31, they may tend to consolidate into a single bubble. When the cartridge cap is being handled during removal of closure cap 32', pressure on tube 22 may cause a slight ejection of sterilant at 30a. At this point it is to be noted that FIGS. 7-12 have been presented in a vertical attitude for convenience of illustration, but in use the parts can be oriented in any desired attitude.

When the male Luer member 24 is being mounted on female Luer member 19 (FIG. 9), the sterilant 30a will coat the thread areas 42 and 45 and surfaces 38 and 39. Furthermore, during the initial stages of mounting, there will be air or liquid trapped in area 55 (FIG. 9), and as the male member 37 threads onto the female portion 43, there will be a slight compression of the air in bubble 31. This is especially the case because there is incompressible dialysis liquid 57 in tube 14. Liquid 57 is depicted by dash lines for illustration purposes. At this time O-ring 47 has not yet been compressed, and it is in the position shown in FIG. 9 proximate the base of frustoconical portion 51. However, as the male member 24 moves onto female member 19 to the position shown in FIG. 10, there is still more compression of the air in bubble 31, and O-ring 47 moves onto frustoconical portion 51. When cap 10 is in its fully seated position with the outside surface 39 of male member 37 is in a first inner sealed engagement with surface 38 of connector 19, O-ring 47 is compressed after having moved from its position on neck 43 (FIG. 9) to its position onto frustoconical connector portion 51 (FIG. 10), and O-ring 47 provides a second outer sealed engagement between the end 50 of collar 41 and the surface of frustoconical portion 51. The arrows in FIGS. 9, 11 and 12 depict the movement of the sterilant cartridge cap 10 relative to frustoconical portion 51. The outer seal between rim end 50 and frustoconical portion 51 closes before the inner seal between surfaces 38 and 39.

During the removal of the sterilant cartridge cap 10 from connector 19 on tube 14, as shown in FIG. 11, the O-ring 47 will move toward its position of FIG. 9 from its position of FIG. 10 by sliding along the frustoconical portion 51. However, there will still be a sealing between frustoconical portion 51 and the rim 50 of the male member for the initial portion of the unscrewing travel. However, while this sealing still exists, the external surface 39 of male portion 37 will separate from the internal surface 38 of the female portion of the connector (FIG. 11). During this portion of the unscrewing, there will be a tendency to create a vacuum in zone 55 proximate the end of male member 37 because of the increase of the volume in this area. However, since the O-ring, 47 remains in sealing relationship between rim 50 of male member 24 and frustoconical surface 51, sterilant will be drawn from cartridge cap 10 into zone 55 to fill this vacuum. Furthermore, O-ring 47 maintains the sealing relationship during the initial unscrewing action to prevent environmental air from entering the space between the connector portions 19 and 24 and to prevent this air from being drawn into the area of zone 55, with the attendant possibility of carrying contaminants with it. The movement of sterilant into zone 55 is further promoted because of the expansion of the air in bubble 31 in combination with the aforementioned creation of the vacuum in zone 55. It is also promoted because the atmospheric pressure on the outside of cartridge cap tube 22, which is softer than extension set tube 14, applies pressure thereon to force sterilant therefrom thereby coating the internal surface of the female Luer lock portion 43. The atmospheric pressure on the outside of tube 22 causes the foregoing action because it is greater than the air pressure, namely, the vacuum in zone 55. The foregoing action of ejecting sterilant during unscrewing separation of the Luer lock has been observed, and it is believed to occur because of the foregoing reasons. In addition, it is believed to occur because the sterilant cap 10 has been resting against the user's abdomen since the last infusion, and thus it has been warmed to body temperature, which is above the ambient temperature at which the sterilant cap 10 was installed. This increase in temperature causes the air bubble 31 and sterilant 30 to tend to expand which increases the pressure within tube 22. However, it cannot expand while the Luer lock is closed tight. Therefore, when the cartridge cap 10 is moved to the position of FIG. 11, the increase in pressure in tube 22 will also aid the above-described ejection of sterilant 30 into zone 55.

In FIG. 11 the air bubble 31 is shown expanded after surface 38 has separated from surface 39 and there has been a flow of sterilant from the cartridge cap 10 into the female portion of the Luer lock. The foregoing action of ejecting sterilant into zone 55 is advantageous in that the sterilant is ejected into this zone and into the space within collar 41 rather than air being drawn into the area within collar 41 due to the creation of the vacuum in zone 55. In the past, in caps which did not have the adjustable seal provided by the O-ring in the above-described manner, as complemented by the air bubbles such as 31 and a softer tubular body such as 22, when the seal between members 37 and 43 was broken, it was air rather than sterilant which was drawn into the area within collar 41 with the attendant possibility of contamination by air-borne organisms.

In FIG. 13 a further embodiment of the present invention is disclosed. This embodiment differs from the preceding embodiments in that the female connector 19 and the male connector 24 are reversed. More specifically, the female connector 19, which is identical to the female connector of FIGS. 7-12, is attached to tube 22 of sterilant cartridge cap 60 whereas the male connector 24, which is identical to the male connector 24 shown in FIGS. 7-12, is mounted on the end of the extender tube 14. The O-ring 47 is mounted on neck 43, as in FIGS. 7-12. The advantage of the foregoing change is that the O-ring 47 will not accumulate BETADINE or other foreign material which might be objectionable because the sterilant cap 60 with the O-ring 47 mounted thereon is thrown away after each use. Aside from the foregoing reversal of connectors 19 and 24, the parts operate in exactly the same manner as discussed above relative to FIGS. 7-12.

In FIGS. 14-16 an additional embodiment of the present invention is disclosed. In this embodiment the O-ring 47 of the previous embodiments is eliminated but the parts still provide the double seal described above. In the embodiment as shown in FIGS. 14, 15 and 16, the female Luer connector 19 is identical to that described in FIGS. 7-12. However, the male connector 24' has been changed in that its collar 41' is fabricated of soft plastic material so that when it is fully tightened, its end portion 61 expands from the normal unstressed cylindrical condition of FIG. 16 and forms a seal with frustoconical member 51 after the male member 37' is in sealed arrangement with surface 38 within neck 43, as shown in FIG. 14. When the cartridge cap 70 is moved in the direction of arrow 62 (FIG. 15), the inner seal between neck portion 43 and male member 37' will be broken while the outer seal between end 61 and frustoconical portion 51 will be maintained, thereby providing the same action described above by the O-ring of FIGS. 7-12, and thus sterilant is drawn from the cartridge cap 70 into the zone 55' as a result of vacuum created therein. It is to be especially noted that all parts of the embodiment of FIGS. 14-16 are identical to those described above relative to FIGS. 7-12 except for the parts which have been specifically described as being different. In FIG. 16 the male connector 24' is shown as having moved to a position wherein the outer seal between end 61 and frustoconical member 51 has been broken and the flexible resilient collar 58' has returned to its normal undistorted condition from its expanded condition of FIG. 14.

The connector 24' can merely have the collar 41' as softer resilient plastic material while the remainder of the connector is of hard plastic or it may also have the male member portion 37' also fabricated of soft plastic. At this point it is to be noted that wherever primed numerals are used, they represent modifications of previously described structure having unprimed numerals.

Figure 17:
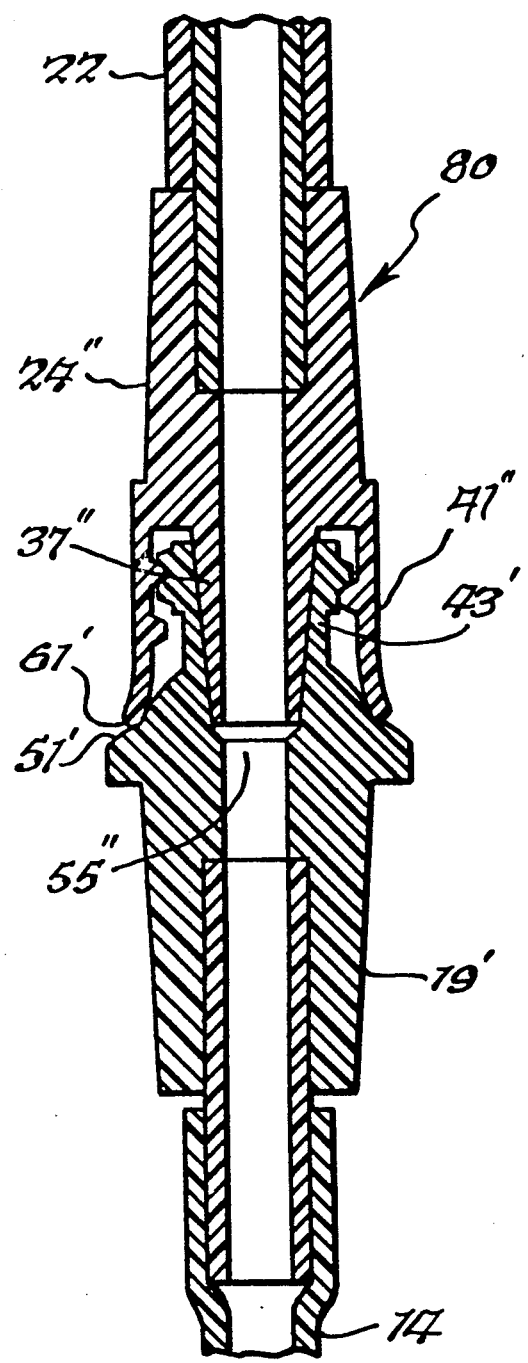
FIG. 17 is a fragmentary cross sectional view of still another embodiment wherein both the male and female Luer connectors are fabricated of flexible resilient material.

In FIG. 17 a still further embodiment of the present invention is disclosed. This embodiment differs from the embodiment of FIGS. 14-16 in that both the male connector 24" and the female connector 19' are both fabricated of soft plastic material so that the end 61' of collar 58", which expands in the same manner as shown in FIG. 14, also compresses the frustoconical portion 51' of soft member 19' thereby providing a good seal. The embodiment of FIG. 17 operates in the same manner as described above relative to the embodiment of FIGS. 14-16 in that the inner seal between male member 37" and neck 43 is broken before the outer seal between tip 61' and frustoconical portion 51' is broken to thereby create a vacuum in zone 55". Aside from the fact that both the connector 19' and the connector 24" are fabricated of soft plastic material which is flexible and resilient, the remainder of the parts of the cartridge cap 80 are identical to that described relative to FIGS. 7-16. Also, as an alternative, the collar 41" can be made of hard plastic and it can dig into a soft resilient frustoconical portion 51' so as to maintain a seal therewith after the seal between parts 37" and 43' is broken.

Further relative to the embodiments of FIGS. 14-17, it will be appreciated that the male and female connectors may be reversed as discussed above relative to FIG. 13.

While the preceding description has been primarily directed to peritoneal dialysis, it will be appreciated, as noted above, that the improved sterilant cartridge-cap has universal usage in any application wherein inline sterilant delivery is required. Also, while all embodiments have shown the sterilant tube such as 22 being preferably cylindrical and of uniform cross section, it will be appreciated that it can be of any desired configuration.

It can thus be seen that the sterilant cartridge-cap 10 of the present invention and the associated connector end of a tube such as the extension set 11 are manifestly capable of achieving the above-enumerated objects and while preferred embodiments of the present invention have been disclosed, it will be appreciated that it is not limited thereto but may be otherwise embodied within the scope of the following claims.

What is claimed is:

1. A sterilant cartridge-cap connector assembly comprising a sterilant cartridge cap including a tubular body member having first and second ends, flexible sidewall means on said tubular body member for receiving digital pressure, means sealing said first end, first connector means on said second end, second connector means for attachment to said first connector means, sterilant liquid means in said tubular body member for transfer to said second connector means upon the application of said digital pressure to said flexible sidewall means, inner seal means for providing a first seal between said first and second connector means, and outer seal means for providing a second seal between said first and second connector means when said first connector means is mounted onto said second connector means, said inner and outer seal means being dimensioned to maintain said second seal closed while said first seal is being opened during uncoupling of said first and second connector means to thereby cause a flow of said sterilant liquid means from said first connector means into said second connector means as a result of a vacuum created proximate said inner seal means during said uncoupling.

2. A sterilant cartridge-cap connector assembly as set forth in claim 1 wherein said second seal means includes a shoulder on one of said first and second connector means, and a collar including a rim on the other of said first and second connector means.

3. A sterilant cartridge-cap connector assembly as set forth in claim 2 wherein said second seal means includes an O-ring between said rim and said shoulder.

4. A sterilant cartridge-cap connector assembly as set forth in claim 3 wherein said shoulder is of frustoconical configuration.

5. A sterilant cartridge-cap connector assembly as set forth in claim 4 including a tubular portion on said second connector means, said O-ring being of a dimension to be contracted onto said tubular portion when said second connector means is not connected to said first connector means, and said O-ring being in a stretched condition and located on said frustoconical shoulder when said outer seal means is in fully sealed relationship.

6. A sterilant cartridge-cap connector assembly as set forth in claim 2 wherein said rim is flexible and resilient for effecting said second sealing relationship with said shoulder.

7. A sterilant cartridge-cap connector assembly as set forth in claim 2 wherein both said rim and said shoulder are flexible and resilient.

8. A sterilant cartridge-cap connector assembly as set forth in claim 1 wherein said second connector means is connected to a member which requires more force to compress than the force required to compress said flexible sidewall means of said tubular body member.

9. A sterilant cartridge-cap connector assembly as set forth in claim 1 including gas bubble means in said sterilant liquid means.

10. A sterilant cartridge-cap connector assembly as set forth in claim 9 wherein said tubular body member is fabricated of clear plastic to provide a visual indication of movement of said sterilant liquid means on application of said digital pressure to said flexible tubular member.

11. A sterilant cartridge-cap connector assembly as set forth in claim 10 wherein said sterilant liquid means comprises a clear substantially colorless non-staining liquid.

12. A sterilant cartridge-cap connector assembly as set forth in claim 1 wherein said inner and outer seals are dimensioned to close said second seal prior to closing said first seal during the mounting of said first connector means onto said second connector means.

13. A sterilant cartridge-cap connector assembly as set forth in claim 12 including gas bubble means in said sterilant liquid means.

14. A sterilant cartridge-cap connector assembly comprising a sterilant cartridge cap including a flexible tubular body member having first and second ends, sidewall means on said flexible tubular member for receiving digital pressure, means sealing said first end, first connector means on said second end, second connector means for attachment to said first connector means, sterilant liquid means in said tubular body member for transfer to said second connector means upon the application of said digital pressure to said sidewall means, one of said first and second connector means comprising a male Luer connector including a central male member and a spaced collar containing an internal thread, the other of said first and second connector means including a female Luer connector having an external thread for mating with said internal thread of said spaced collar and having a tubular extension having an open end for receiving said central male member in a first sealing relationship, a shoulder on said tubular extension, a rim on the end of said collar, and resilient seal means on said female Luer connector for being sandwiched between said shoulder and said rim for providing a second sealing relationship when said male Luer connector is screwed on to said female Luer connector, said resilient seal means being of a dimension to establish said second sealing relationship before said first sealing relationship is established and to maintain said second sealing relationship after said first sealing relationship is broken during unscrewing of said male and female Luer connectors to thereby cause a flow of said sterilant liquid means from said first connector means into said second connector means as a result of a vacuum created between said male and female Luer connectors during said unscrewing.

15. A sterilant cartridge-cap connector assembly as set forth in claim 14 wherein said shoulder is of frustoconical configuration, and wherein said resilient seal means is stretched and moved onto said shoulder of frustoconical configuration incidental to the screwing of said male Luer connector onto said female Luer connector.

16. A sterilant cartridge-cap connector assembly as set forth in claim 15 wherein said resilient seal means comprises an O-ring which contracts and moves on said frustoconical shoulder toward said tubular extension during said unscrewing to maintain said second sealing relationship.

17. A sterilant cartridge-cap connector assembly as set forth in claim 16 including annular ridge means on said tubular extension for retaining said O-ring in position proximate said shoulder when said male and female Luer connectors are not connected.

18. A sterilant cartridge-cap connector assembly comprising a sterilant cartridge cap including a flexible tubular body member having first and second ends, sidewall means on said flexible tubular member for receiving digital pressure, means sealing said first end, first connector means on said second end, second connector means for attachment to said first connector means, sterilant liquid means in said tubular body member for transfer to said second connector means upon the application of said digital pressure to said sidewall means, one of said first and second connector means comprising a male Luer connector including a central male member and a spaced collar containing an internal thread, the other of said first and second connector means including a female Luer connector having an external thread for mating with said internal thread of said spaced collar and having a tubular extension having an open end for receiving said central male member in a first sealing relationship, a shoulder on said tubular extension, a rim on the end of said collar, and resilient seal means on said female Luer connector for being sandwiched between said shoulder and said rim for providing a second sealing relationship when said male Luer connector is screwed on to said female Luer connector, one of said first and second connector means being mounted on a tube having a first hardness, and said flexible tubular body member having a second hardness which is less than said first hardness, said seal means being of a dimension to establish said second sealing relationship before said first sealing relationship is established and to maintain said second sealing relationship after said first sealing relationship is broken during unscrewing of said first an second connector means to thereby cause a flow of said sterilant liquid means from said first connector means into said second connector means as a result of a vacuum created therebetween during said unscrewing.

19. A sterilant cartridge-cap connector assembly comprising a sterilant cartridge cap including a flexible tubular body member having first and second ends, sidewall means on said flexible tubular member for receiving digital pressure, means sealing said first end, first connector means on said second end, second connector means for attachment to said first connector means, sterilant liquid means in said tubular body member for transfer to said second connector means upon the application of said digital pressure to said sidewall means, one of said first and second connector means comprising a male Luer connector including a central male member and a spaced collar containing an internal thread, the other of said first and second connector means including a female Luer connector having an external thread for mating with said internal thread of said spaced collar and having a tubular extension having an open end for receiving said central male member in a first sealing relationship, a shoulder on said tubular extension, a rim on the end of said collar, and resilient seal means on said female Luer connector for being sandwiched between said shoulder and said rim for providing a second sealing relationship when said male Luer connector is screwed on to said female Luer connector, and gas bubble means in said sterilant liquid means, said resilient seal means being of a dimension to establish said second sealing relationship before said first sealing relationship is established and to maintain said second sealing relationship after said first sealing relationship is broken during unscrewing of said male and female Luer connectors to thereby cause a flow of said sterilant liquid means from said first connector means into said second connector means as a result of a vacuum created between said male and female Luer connectors during said unscrewing.

20. A sterilant cartridge-cap connector assembly as set forth in claim 19 wherein said shoulder is of frustoconical configuration, wherein said resilient seal means is stretched and moved onto said shoulder of frustoconical configuration incidental to the screwing of said male Luer connector onto said female Luer connector.

21. A sterilant cartridge-cap connector assembly as set forth in claim 9 wherein said tubular body member is fabricated of clear plastic to provide a visual indication of movement of said sterilant liquid means on application of said digital pressure to said flexible tubular member.

22. A sterilant cartridge-cap connector assembly as set forth in claim 21 wherein said sterilant liquid means comprises a clear substantially colorless non-staining liquid.

* * * * *

UNITED STATES PATENT AND TRADEMARK OFFICE
CERTIFICATE OF CORRECTION

PATENT NO. : 5,195,957
DATED : March 23, 1993
INVENTOR(S) : Dennis R. Tollini It is certified that error appears in the above-identified patent and that said Letters Patent is hereby corrected as shown below:

Title page, item [57]
In the Abstract, line 8, change "form" to --from--.
Title page, item [57]
In the Abstract, line 10, change "mal" to --male--.

Column 12, line 13 (claim 18), change "an" to --and--.

Column 12, line 54 (claim 20), before "wherein" insert --and--.

Column 12, line 59 (claim 21), change "9" to --19--.

Signed and Sealed this

Ninth Day of November, 1993

*Attest:*

BRUCE LEHMAN

*Attesting Officer*     *Commissioner of Patents and Trademarks*